US011484375B2

(12) United States Patent
Xu et al.

(10) Patent No.: US 11,484,375 B2
(45) Date of Patent: Nov. 1, 2022

(54) INTEGRATED CONTROL SYSTEM FOR A SURGICAL ROBOT BASED ON EMBEDDED COMPUTERS

(71) Applicant: Beijing Surgerli Technology Co., Ltd., Beijing (CN)

(72) Inventors: Kai Xu, Beijing (CN); Bin Zhao, Beijing (CN); Zhengchen Dai, Beijing (CN); Jiangran Zhao, Beijing (CN); Huan Liu, Beijing (CN); Wukun Mei, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 774 days.

(21) Appl. No.: 16/289,521

(22) Filed: Feb. 28, 2019

(65) Prior Publication Data
US 2019/0192243 A1    Jun. 27, 2019

Related U.S. Application Data

(63) Continuation of application No. PCT/CN2017/099849, filed on Aug. 31, 2017.

(30) Foreign Application Priority Data

Aug. 31, 2016 (CN) .......................... 201610799299.0

(51) Int. Cl.
*A61B 34/00* (2016.01)
*A61B 34/30* (2016.01)
(Continued)

(52) U.S. Cl.
CPC .............. *A61B 34/35* (2016.02); *A61B 34/25* (2016.02); *A61B 34/30* (2016.02); *A61B 34/74* (2016.02);
(Continued)

(58) Field of Classification Search
CPC ......... A61B 34/74; A61B 34/37; A61B 34/35; A61B 34/25; A61B 90/37; A61B 34/30;
(Continued)

(56) References Cited

U.S. PATENT DOCUMENTS

2009/0326552 A1   12/2009  Diolaiti
2010/0228264 A1   9/2010   Robinson et al.
(Continued)

FOREIGN PATENT DOCUMENTS

CN    101321606 A    12/2008
CN    102697553 A    10/2012
(Continued)

OTHER PUBLICATIONS

International Search Report of PCT/CN2017/099849.
The first Office Action of CN application 2016107992990.
The search report of EP appiication 178455010.

*Primary Examiner* — Khoi H Tran
*Assistant Examiner* — Tanner L Cullen
(74) *Attorney, Agent, or Firm* — Bayes PLLC (57) ABSTRACT

A control system for a surgical robot is provided. The control system includes a first embedded computer and a second embedded computer configured to receive status information from the first embedded computer. The status information includes a status of zero-return for a surgical tool driving module or an imaging tool driving module. The control system also includes a host computer configured to receive the status information from the second embedded computer. The surgical tool driving module or the imaging tool driving module includes a controller, a motor connected with a first coupling and configured to drive the surgical tool or an imaging tool, and a zero point switch configured to detect whether the first coupling is at a zero position. The controller is configured to transmit the status of zero-return to the first embedded computer based on whether the first coupling is at the zero position.

20 Claims, 4 Drawing Sheets

(51) Int. Cl.
  *B25J 9/16* (2006.01)
  *A61B 34/35* (2016.01)
  *A61B 90/00* (2016.01)
  *A61B 90/98* (2016.01)
  *B25J 13/04* (2006.01)
  *B25J 13/06* (2006.01)

(52) U.S. Cl.
  CPC .............. *A61B 90/37* (2016.02); *A61B 90/98* (2016.02); *B25J 9/1689* (2013.01); *B25J 13/04* (2013.01); *B25J 13/06* (2013.01); *A61B 2034/303* (2016.02)

(58) Field of Classification Search
  CPC ... A61B 34/70; A61B 90/98; A61B 2034/303; A61B 2034/2059; A61B 2017/00477; B25J 9/1689; B25J 13/06
  See application file for complete search history.

(56) References Cited

U.S. PATENT DOCUMENTS

| | | | |
|---|---|---|---|
| 2012/0059390 A1* | 3/2012 | Mintz | A61B 34/37 606/130 |
| 2013/0023860 A1* | 1/2013 | Nagashimada | A61B 34/70 606/1 |
| 2013/0325034 A1 | 12/2013 | Schena et al. | |
| 2014/0128886 A1* | 5/2014 | Holop | A61B 18/14 606/130 |
| 2014/0257330 A1* | 9/2014 | Choi | A61B 34/37 606/130 |
| 2014/0276951 A1* | 9/2014 | Hourtash | A61B 34/37 606/130 |
| 2016/0066815 A1 | 3/2016 | Mei et al. | |
| 2018/0000543 A1* | 1/2018 | Hibner | A61B 34/20 |
| 2018/0071860 A1* | 3/2018 | Odakura | B23K 20/22 |
| 2021/0275212 A1* | 9/2021 | Morrissette | A61M 39/06 |

FOREIGN PATENT DOCUMENTS

| | | | | |
|---|---|---|---|---|
| CN | 102834064 A | 12/2012 | | |
| CN | 103930064 A | 7/2014 | | |
| CN | 104105577 A | 10/2014 | | |
| CN | 104334111 A | 2/2015 | | |
| CN | 104640514 A | 5/2015 | | |
| CN | 105078576 A | 11/2015 | | |
| CN | 16289521 A | 2/2019 | | |
| DE | 102014005351 A1 * | 10/2015 | ............ | G01B 11/24 |
| EP | 2942029 A1 | 11/2015 | | |
| WO | 2007005555 A2 | 1/2007 | | |
| WO | 2011142165 A1 | 11/2011 | | |

* cited by examiner

INTEGRATED CONTROL SYSTEM FOR A SURGICAL ROBOT BASED ON EMBEDDED COMPUTERS

CROSS-REFERENCE TO RELATED APPLICATIONS

The present application is a continuation of PCT Application No. PCT/CN2017/099849, filed on Aug. 31, 2017, which claims the priority to Chinese Patent Application No. 201610799299.0, entitled "an integrated control system for a surgical robot based on embedded computers", filed on Aug. 31, 2016, the disclosure of which is incorporated herein by reference. The entire text thereof is incorporated herein by reference.

TECHNICAL FIELD

The invention relates to a medical instrument control system, in particular to an integrated control system for a surgical robot based on embedded computers.

BACKGROUND TECHNIQUE

In the modern medical field, manual porous laparoscopic minimally invasive surgeries have been widely used in clinical practice. Such minimally invasive surgeries have successfully reduced postoperative pain, probability of complications, recovery time for the patient and improved postoperative scarring. In recent years, robot-assisted porous laparoscopic minimally invasive surgeries have been widely used for the convenience of doctors and better postoperative outcomes. Among them, Da Vinci surgery robot system provided by Intuitive Surgical (American Intuition Surgery) can assist doctors in the completion of porous laparoscopic minimally invasive surgery and has achieved great commercial success.

In order to further reduce the surgical trauma area and recovery time, some researchers proposed single-hole laparoscopic minimally invasive surgeries. Compared to multiple body surface incisions required in a porous laparoscopic minimally invasive surgery, all surgical tools in a single-hole laparoscopic minimally invasive surgery are inserted into the abdominal cavity via a single body surface incision (usually the navel), further reducing trauma to the patient. However, the configuration of such a single inlet places higher demands on both of the design of the surgical instruments and the operation of the doctor at the time of surgery. Manual single-hole laparoscopic surgeries based on traditional rigid surgical tools have not been widely used in clinical practice due to the reasons such as complicated hand-eye coordination operation requirements, the limited flexibility of the surgical tools and the small working range.

By rationally planning and designing the single-hole laparoscopic surgical robot system, the problems existing in manual single-hole laparoscopic surgery can be effectively solved, and the existing single-hole laparoscopic surgical robot system technical solutions have not yet matured.

SUMMARY OF THE INVENTION

In view of the above problems, an object of the present invention is to provide an imaging tool and a surgical tool control system for a surgical robot, which can effectively solve the problem that manual single-hole laparoscopic surgery cannot be widely used in clinical practice.

In order to achieve the above object, the present invention adopts the following technical solution: an integrated control system for a surgical robot based on embedded computers, the system includes a main control terminal and a controlled terminal, the main control terminal and the controlled terminal perform exchange of control information and status information; the main control terminal comprises a remote control device, a host computer and pedals; the remote control device and the pedals are connected with the host computer; when the pedal is depressed, the remote control device controls motions of a certain tool with which a mapping relationship is established; when the pedal is released, the corresponding motion control is cut off; wherein the certain tool includes a surgical tool or an imaging tool; the controlled terminal includes a control cabinet, the surgical tool, a surgical actuator, the imaging tool, surgical tool driving modules, an imaging tool driving module, and an imaging illumination module; the host computer exchanges the control signals and the status signals with the controlled terminal through the control cabinet; the control cabinet is used to implement an overall switching of the status for the integrated control system, control actions of the surgical tool driving modules and the imaging tool driving module; the surgical tool driving module drives the body of the surgical tool and the surgical actuator carried by the surgical tool to move, and drives the surgical actuator to act, the imaging tool driving module drives the body of the imaging tool and the imaging illumination module carried by the imaging tool to move.

Preferably, the main control terminal further comprises a display and a console, the display is connected with the host computer to display an operation interface, the operation interface can display image signals transmitted back by the controlled terminal and receive operating inputs from an operator; the host computer is disposed on the console.

Preferably, the controlled terminal further comprises indicator lights, an indicator light for imaging, a sterile barrier, a multi-lumen tube and a base; the display status of the indicator lights and the indicator light for imaging is controlled by the control cabinet, the sterile barrier is used to isolate a sterile portion of the controlled terminal from a remaining non-sterile portion thereof; the imaging tool driving module and the surgical tool driving modules are secured on the base, the multi-lumen tube is secured on the base through the sterile barrier.

Preferably, the control cabinet comprises a local area network router, an embedded computer for surgical tool, an embedded computer for imaging, and an embedded computer; when the embedded computer is used to the overall switching of the status of the integrated control system, the embedded computer receives signals transmitted by the host computer, the embedded computer for surgical tool, the embedded computer for imaging via the local area network router, and receives the signal transmitted and received by the embedded computer for the surgical tool, the embedded computer for imaging via a first communication bus connected with the embedded computer for surgical tool, the embedded computer for imaging, and updates the current status of the integrated control system according to the signals received by the embedded computer.

Preferably, when the embedded computer is used to control the display status of the indicator lights and the indicator light for imaging, the embedded computer is connected with the indicator lights and the indicator light for imaging through a third communication bus, and controls the display status of the indicator lights and the indicator light for imaging, the indicator lights and the indicator light for imaging are disposed on the corresponding surgical tool driving modules and imaging tool driving module, respectively, for indicating their corresponding statuses.

Preferably, the controlled terminal further comprises an electromagnetic relay and an energy generator, the embedded computer controls the On/Off of the electromagnetic relay via a fourth communication bus, thereby when controlling the enabling and mode switching of the energy generator, the energy generator can correspondingly control the energy surgery actuator connected thereto, so as to achieve the On/Off of the energy input and the mode switching of the input energy.

Preferably, the controlled terminal further includes an image display, an electromagnetic relay and an energy generator; the surgical tool driving modules and the imaging tool driving module are both further provided with a control module, a reading chip, a motor and a first coupling; the surgical tools and the imaging tool are both provided with an information tag and a second coupling; the embedded computer for surgical tool and the embedded computer for imaging communicate with the reading chips in the surgical tool driving modules and the imaging tool driving module through a second communication bus; the reading chips are connected with the information tags in the surgical tools and the imaging tool, for identifying and reading the information tags; the embedded computer for surgical tool and the embedded computer for imaging send signals to the control modules in the surgical tool driving modules and the imaging tool driving module through the first communication bus, each of the control modules thus drives the corresponding motor connected thereto and the first coupling tightly connected with the output axis of the motor to rotate, each of the first couplings is connected with the second coupling in the surgical tools and the imaging tool via the sterile barrier, respectively, and drives the second coupling to rotate, thereby driving the body of the surgical tool and the surgical actuator carried by the surgical tool to move based on posture information included in the signals received by the control module and driving the body of the imaging tool and the imaging illumination module carried by the imaging tool to move based on posture information included in the signals received by the control module.

Preferably, the surgical tool driving modules and the imaging tool driving module are further provided with a zero point switch and a motor rotation angle sensor; the motor rotation angle sensor is connected with the motor, and transmits the detected rotation angle position information for an output axis of the motor to the control module in real time; the zero point switch detects whether the first coupling is turned to a zero position by using an identification provided on the first coupling, and feeds the information back to the control module.

Preferably, the surgical actuator is a mechanical surgical actuator or/and an energy surgical actuator.

Preferably, the remote control device is further provided with a trigger device; when the trigger device is triggered, the host computer reads a status-changed signal of the trigger device, and transmits the status-changed signal to the embedded computer for surgical tool or the embedded computer, the embedded computer for surgical tool controls actions of the respective motor by the control module in the surgical tool driving modules, thereby implementing the action controls of the mechanical surgical actuator; the embedded computer controls the On-Off and mode switching of the energy generator with the electromagnetic relay to achieve On and mode switching of an energy input for the energy surgical actuator.

Preferably, the indicator lights and the indicator light for imaging are used to display operating statuses of the surgical tool and the surgical tool driving modules, the imaging tool and the imaging tool driving module, when the indicator lights and the indicator light for imaging are in the following colors: yellow indicates a pre-installation phase of the surgical tool/imaging tool; green indicates the preparation/working phase of the surgical tool/imaging tool; blue indicates the energy generation phase, which indicates that the energy generator is outputting energy to the energy surgical actuator; red indicates that an error has occurred and a manual debugging phase is entered.

Preferably, the number of the surgical tool driving modules is three: first to third surgical tool driving modules; the number of the surgical tools is three: first to third surgical tools; the number of the surgical actuators is three: first to third surgical actuators; the number of the indicator lights is three: first to third indicator lights; the number of the embedded computers for surgical tools is three: first to third embedded computers for surgical tools; the number of the remote control devices is two: a first remote control device and a second remote control device; the number of the pedals is two: a first pedal and a second pedal; the number of the trigger devices is two: a first trigger device and a second trigger device.

The invention also provides an integrated control system for a surgical robot, the system comprising: a main control terminal and a controlled terminal, the main control terminal and the controlled terminal perform exchange of control information and status information; the main control terminal comprises a control device, a host computer and a selector; the control device and the selector are both connected with the host computer; the selector is used to select an object to be controlled by the control device; wherein the object comprises a surgical tool or an imaging tool; the controlled terminal includes a control unit, surgical tool driving modules, the surgical tool, a surgical actuator, an imaging tool driving module, the imaging tool and an imaging illumination module; the host computer exchanges the control signals and the status signals with the controlled terminal through the control unit; the control unit is used to implement an overall switching of the status for the integrated control system, control the surgical tool driving modules and the imaging tool driving module; the surgical tool driving module is used to drive the surgical tool and the surgical actuator carried by the surgical tool, the imaging tool driving module is used to drive the imaging tool and the imaging illumination module carried by the imaging tool.

Preferably, the main control terminal further comprises a display and a console, the display is connected with the host computer to display an operation interface and receive operating inputs from an operator; the operation interface can also display image signals transmitted back by the controlled terminal; the host computer is disposed on the console.

Preferably, the control unit comprises a local area network router, an embedded computer for surgical tool, an embedded computer for imaging, and an embedded computer; the embedded computer, the embedded computer for surgical tool and the embedded computer for imaging perform data exchange with the host computer via the local area network route, the embedded computer, the embedded computer for surgical tool and the embedded computer for imaging perform data exchange via a first communication bus and/or the local area network route, the embedded computer updates the status of the integrated control system based on the received signals.

Preferably, the controlled terminal further comprises indicator lights, an indicator light for imaging, a sterile barrier, a multi-lumen tube and a base; the display status of the indicator lights and the indicator light for imaging is controlled by the control unit, the sterile barrier is used to isolate a sterile portion of the controlled terminal from a remaining non-sterile portion thereof; the imaging tool driving module, the surgical tool driving modules and the multi-lumen tube are secured on the base.

Preferably, the embedded computer is connected with the indicator lights and the indicator light for imaging through a third communication bus so as to control the display status of the indicator lights and the indicator light for imaging, the indicator lights and the indicator light for imaging are disposed on the corresponding surgical tool driving modules and imaging tool driving module, respectively, for indicating their corresponding statuses.

Preferably, the controlled terminal further comprises an electromagnetic relay and an energy generator, the energy generator can be used to connect the energy surgery actuator, the embedded computer controls the electromagnetic relay via a fourth communication bus, thus controlling the enabling and mode switching of the energy generator, thereby the energy generator can correspondingly control the energy surgery actuator connected thereto, so as to achieve the On/Off of the energy input and the mode switching of the input energy.

Preferably, the surgical tool driving modules and the imaging tool driving module are respectively provided with a control module, a reading chip, a motor and a first coupling that is connected fitly with the motor; the surgical tools and the imaging tool are both provided with an information tag and a second coupling that is connected fitly with the first coupling; the embedded computer for surgical tool and the embedded computer for imaging communicate with the reading chips in the surgical tool driving modules and the imaging tool driving module through a second communication bus, respectively; each of the reading chips is connected with corresponding information tags, respectively, for identifying and reading the information tags; the embedded computer for surgical tool and the embedded computer for imaging send signals to the control modules in the surgical tool driving modules and the imaging tool driving module through the first communication bus, respectively, each of the control modules is used to drive the corresponding motor connected thereto so as to achieve the driving of the corresponding surgical tool, imaging tool, surgical actuator and/or imaging illumination module.

Preferably, the concrete manner in which the corresponding surgical tool, imaging tool, surgical actuator and/or imaging illumination module are driven comprises: each of the control modules driving the corresponding motor connected thereto and the first coupling tightly connected with the output axis of the motor to rotate, each of the first couplings is respectively connected with the surgical tool, the second coupling in the imaging tool through the sterile barrier and drives the second coupling to rotate, thereby driving the body of the surgical tool and the surgical actuator carried by the surgical tool to move based on the posture information included in the signal received by the control module, driving the body of the imaging tool and the imaging illumination module carried by the imaging tool to move based on the posture information included in the signal received by the control module.

Preferably, the surgical tool driving modules and the imaging tool driving module are both provided with a zero point switch and a motor rotation angle sensor; the motor rotation angle sensor is used to detect rotation angle position information of the output axis of the corresponding motor, and transmit the information to the control module in real time; the zero point switch is used to detect whether the corresponding first coupling is turned to the zero point position, and feed the information back to the control module.

Preferably, the surgical actuator is a mechanical surgical actuator or/and an energy surgical actuator.

Preferably, the control device is further provided with a trigger device; when the trigger device is triggered, the host computer reads a status-changed signal of the trigger device, and transmits the status-changed signal to the embedded computer for surgery tool or the embedded computer, the embedded computer for surgical tool controls actions of the respective motor by the control module in the surgical tool driving modules, so as to realize the driving of the mechanical surgical actuator; the embedded computer controls the On-Off and mode switching of the energy generator with the electromagnetic relay to achieve On and mode switching of an energy input for the energy surgical actuator.

Preferably, the indicator lights and the indicator light for imaging are used to display operating statuses of the surgical tool and the surgical tool driving modules, the imaging tool and the imaging tool driving module, the indicator lights and the indicator light for imaging are set as follows:

yellow indicates a pre-installation phase of the surgical tool/imaging tool;

green indicates the preparation/working phase of the surgical tool/imaging tool;

blue indicates the energy generation phase, which indicates that the energy generator is outputting energy to the energy surgical actuator;

red indicates that an error has occurred and a manual debugging phase is entered.

Preferably, the integrated control system includes a plurality of groups of the surgical tool driving modules, and each group has its corresponding surgical tool, surgical actuator and embedded computer for surgical tool; the number of the control devices is two; the number of the selectors is two, and the selection operation is performed in a pedal manner.

As a result of the above technical solution of the present invention, it has the following advantages: 1. the present invention provides an integrated control system for a surgical robot which comprises an imaging tool and a plurality of surgical tools and can be used for single-hole laparoscopic surgery, the control system can effectively improve the control flexibility of surgical tools. 2. The integrated control system of the present invention includes a plurality of computers and driving modules connected to each other for communication, which enables a fast and reliable communication between the main control terminal and the controlled terminal. 3. The present invention proposes two methods for establishing a teleoperation mapping between remote control devices and the imaging tool and the plurality of surgical tools, the first method is to set a mapping selection area in an operation interface on the display, and the second method is to set a plurality of pedals at the main control terminal. 4. The present invention further comprises reading chips and information tags for reading status information of the surgical tools and imaging tool, energy generators for achieving electrosurgical, a zero point switch for achieving accurate and reliable back to zero for the driving modules, so as to ensure the functional integrity of the integrated control system for surgical robot.

DETAILED DESCRIPTION

The present invention will be described in detail below with reference to the accompanying drawings and embodiments. It should be noted that the "first", "second", and "third" referred to in the present invention are only used to distinguish components, and do not represent the degree of importance and the order of installation.

Figure 1:
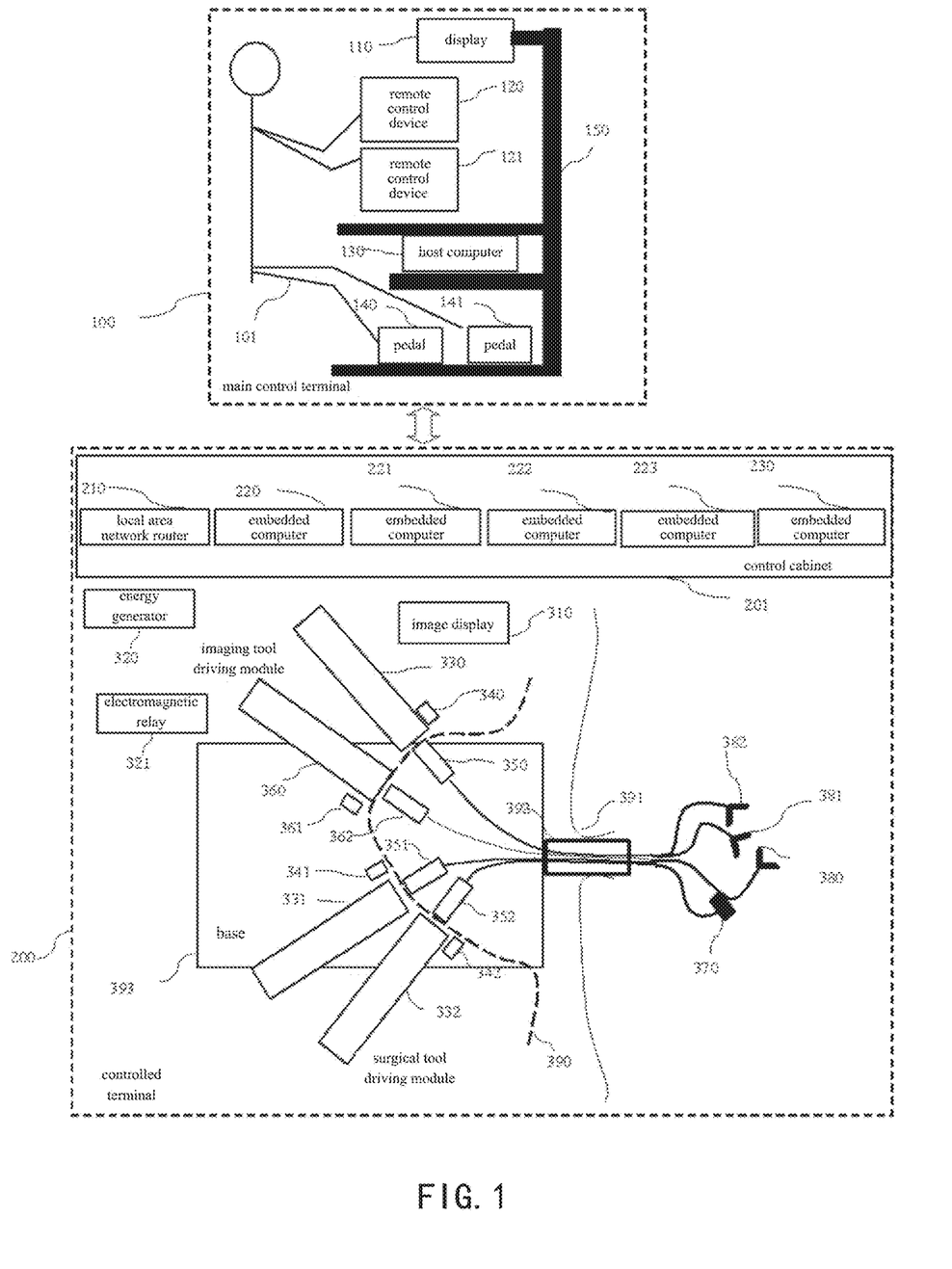
FIG. 1 is a schematic view of an overall structure of the present invention.
Figure 2:
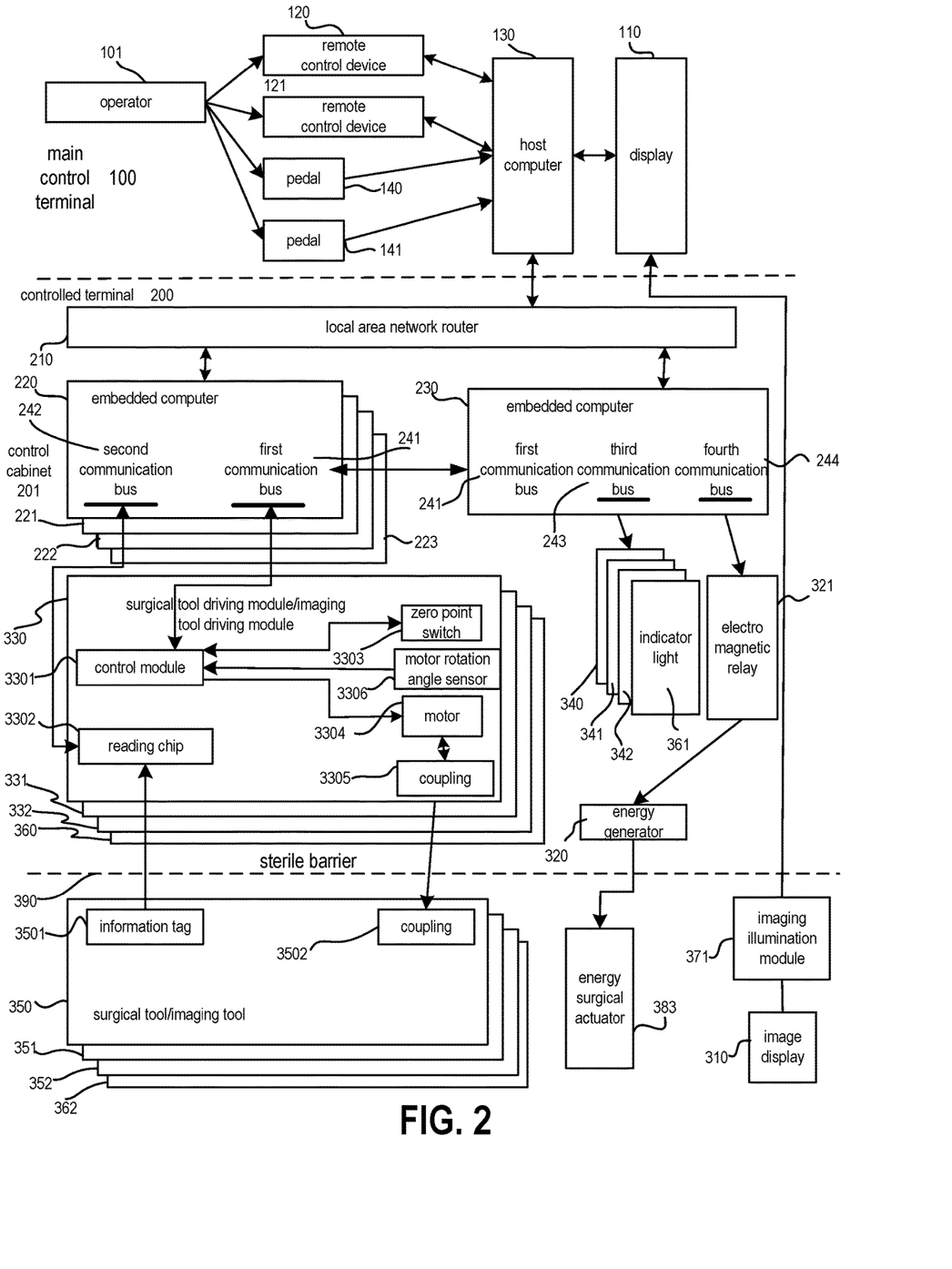
FIG. 2 is a schematic diagram of a signal flow of a control system of the present invention.
Figure 3:
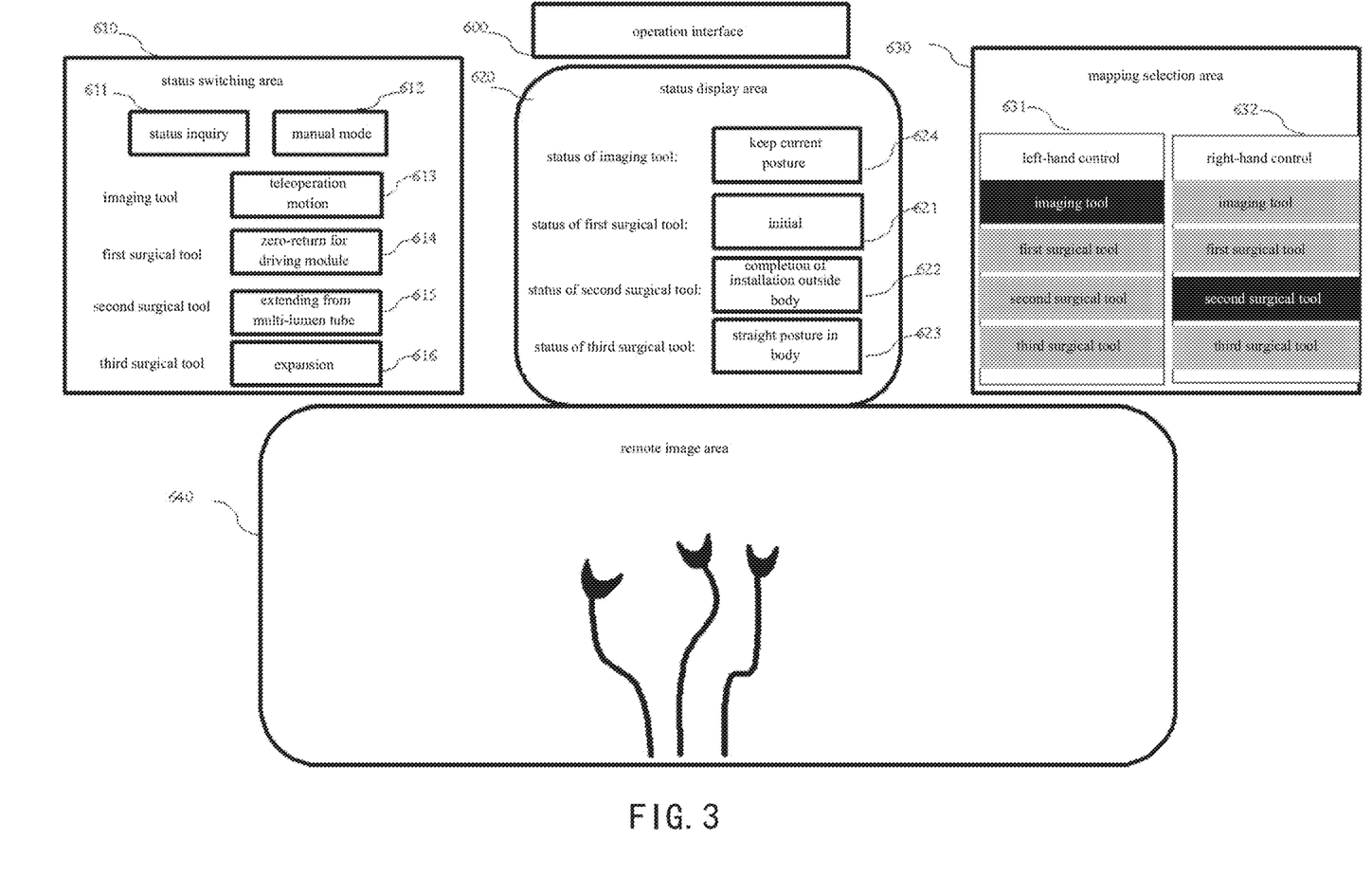
FIG. 3 is a schematic view of an operation interface of the present invention.

As shown in FIG. 1 to FIG. 3, the present invention provides an integrated control system for a surgical robot based on embedded computers, which includes a main control terminal 100 and a controlled terminal 200. The main control terminal 100 and the controlled terminal 200 perform exchange of the control information and the status information.

The main control terminal 100 includes a display 110, a first remote control device 120, a second remote control device 121, a host computer 130, a first pedal 140, a second pedal 141 and a console 150; the display 110 is connected with the host computer 130, the host computer 130 is disposed on the console 150. The first remote control device 120 and the second remote control device 121 are connected with the host computer 130, and transmit the control input to the host computer 130; the first pedal 140 and the second pedal 141 are connected with the host computer 130, and transmit the pedal's signal to the host computer 130, when the first pedal 140 is depressed, the first remote control device 120 controls the motions of a certain tool with which a mapping relationship is established; when the first pedal 140 is released, the corresponding motion control is cut off; the principle of the second pedal 141 is the same as that of the first pedal 140, and details are not described herein again. The host computer 130 exchanges information with the controlled terminal 200 via a network. Wherein, the display 110 is used to display an operation interface 600, the operation interface 600 can display an image signal transmitted back by the imaging illumination module 370 in the controlled terminal 200 and receive an operation input from an operator 101.

As shown in FIG. 1 and FIG. 2, the controlled end 200 includes a control cabinet 201, an image display 310, an electromagnetic relay 321, an energy generator 320, first to third surgical tool driving modules 330-332, first to third indicator lights 340-342, first to third surgical tools 350-352 and first to third surgical actuators 380-382 in the respective surgical tools, an imaging tool driving module 360, an imaging tool 362 and the imaging illumination module 370 therein, an indicator light for imaging 361, a sterile barrier 390, a multi-lumen tube 392 and a base 393. Wherein, the control cabinet 201 includes a local area network router 210, first to third embedded computers 220-222 for surgical tools, an embedded computer 223 for imaging, and an embedded computer 230; each of the first to third surgical tool driving modules 330-332 and the imaging tool driving module 360 is provided with a control module 3301, a reading chip 3302, a zero point switch 3303, a motor 3304, a first coupling 3305 and a motor rotation angle sensor 3306; each of the first to third surgical tools 350-352 and the imaging tool 362 is provided with an information tag 3501 and a second coupling 3502; one or more surgical actuators may employ an energy surgical actuator 383. Wherein:

The local area network router 210 is responsible for transmitting and receiving signals, and is connected to the host computer 130, the first to third embedded computers 220-222 for surgical tools, the embedded computer 223 for imaging, and the embedded computer 230 via Ethernet. The host computer 130 performs exchange of the control signal and status signal with the first to third embedded computers 220-222 for surgical tools, the embedded computer for imaging 223 and the embedded computer 230 via the local area network router 210.

The embedded computer 230 is used to implement an overall switching of the status for the integrated control system of the present invention, control the On/Off of the electromagnetic relay 321 to realize the enabling and mode switching of the energy generator 320, and control display statuses of the first to third indicator lights 340-342 and the indicator light for imaging 361. When the embedded computer 230 is used to the overall switching of the status for the integrated control system, the embedded computer 230 receives signals transmitted by the host computer 130, the first to third embedded computers 220-222 for surgical tools and the embedded computer 223 for imaging through the local area network router 210, and receive signals transmitted by the first to third embedded computers 220-222 for surgical tools and the embedded computer 223 for imaging via a first communication bus 241 (preferably, a controller area network bus, i.e., CAN bus) connected with the first to third embedded computers 220-222 for surgical tools and the embedded computer 223 for imaging, and the current status of the integrated control system is updated based on the received signals. When the embedded computer 230 is used to control the display statuses of the first to third indicator lights 340-342 and the indicator light for imaging 361, the embedded computer 230 is connected with the first to third indicator lights 340-342 and the indicator light for imaging 361 through a third communication bus 243 (preferably a two-wire serial bus, that is, the I2C bus), and controls the display statuses of the first to third indicator lights 340-342 and the indicator light for imaging 361, the first to the third indicator light 340 to 342 and the indicator light for imaging 361 are provided on the corresponding first to third surgical tool driving module 330-332 and the imaging tool driving module 360, respectively, for indicating the respective statuses of the first to third surgical tools 350-352, the first to third surgical tool driving modules 330-332, the imaging tool 362 and the imaging tool driving module 360. When the embedded computer 230 controls the On/Off of the electromagnetic relay 321 via a fourth communication bus 244 (preferably, a serial bus), and thereby controlling the enabling and mode switching of the energy generator 320, the energy generator 320 may correspondingly control the energy surgical actuators 383 connected thereto to achieve the On/Off of the energy input and the mode switching of the input energy (e.g., electrocoagulation, electric cutting, etc.).

The first to third embedded computers 220-222 for surgical tools, the embedded computer 223 for imaging are used to control actions of the first to third surgical tool driving modules 330-332 and the imaging tool driving module 360, respectively. The first to third embedded computers 220-222 for surgical tools and the embedded computer 223 for imaging communicate with the reading chips 3302 in the first to third surgical tool driving modules 330 to 332 and the imaging tool driving module 3302 via a second communication bus 242 (preferably a serial bus); the reading chips 3302 are connected with the information tags 3501 in the first to third surgical tools 350-352 and the imaging tool 362, for identifying and reading the information tags 3501. the first to third embedded computers 220-222 for surgical tools and the embedded computer 223 for imaging can send signals to the control modules 3301 in the first to third surgical tool driving modules 330-332 and the imaging tool driving module 360 via the first communication bus 241, respectively, each of the control modules 3301 thus drives the corresponding motor 3304 connected thereto and the first coupling 3305 tightly connected with the output axis of the respective motors 3304 to rotate, each of the first couplings 3305 is connected with the second coupling 3502 in the first to third surgical tool 350-352 and the imaging tool 362 via the sterile barrier 390, respectively, and drives the second coupling 3502 to rotate, thereby driving the first to third surgical tool 350-352's body and the surgical actuators 380-382 carried by the first to third surgical tool 350-352 to move to a preset posture, driving the imaging tool's body 362 and the imaging illumination module 370 carried thereby to move to a preset posture.

The motor rotation angle sensor 3304 is connected with the motor 3304, and transmits the detected position information of a rotation angle of the output axis of the motor 3304 to the control module 3301 in real time. The zero point switch 3303 can detect whether the first coupling 3305 is turned to the zero point position by using a special identification provided on the first coupling 3305, and feed the information back to the control module 3301. Wherein, the special identification may be a tag made of a highly-reflective material.

The image display 310 is connected with the imaging illumination module 370, and is used to display image signals fed back from the imaging illumination module 370.

The sterile barrier 390 is used to isolate a sterile portion (including the imaging tool 362, the first to third surgical tools 350-352 and the multi-lumen tube 392) of the controlled terminal 200 from a remaining non-sterile portion thereof so as to ensure the clinical feasibility of integrated control system.

The imaging tool driving module 360 and the first to third surgical tool driving modules 330-332 are secured on the base, and the multi-lumen tube 392 is secured on the base 393 through the sterile barrier 390. The multi-lumen tube 392 passes through a single surgical incision 391 on a patient so as to provide passage cavity entering into the abdominal lumen and other auxiliary cavities for the imaging tool 362 and the first to third surgical tools 350-352. The imaging illumination module 370 and the first to third surgical actuators 380-382 both pass through the multi-lumen tube 392 to enter into the human body to implement the signal-hole laparoscopic surgery.

The first to third surgical actuators 380-382 can be mechanical surgery actuators (e.g., clamps, scissors, etc.) or the energy surgical actuator 383 (e.g., electric knife, electric cutting needle or the like).

In the above embodiment, the first remote control device 120 and the second remote control device 121 are respectively provided with a first trigger device and a second trigger device. When the first trigger device or the second trigger device is triggered, the host computer 130 reads a status-changed signal of the first trigger device or the second trigger device, and transmits the status-changed signal to a embedded computer for surgical tool or the embedded computer 230, the embedded computer for surgical tool controls actions of the motor 3304 by the control module 3301 in the surgical tool driving modules, thereby implementing the action controls of the mechanical surgical actuator; the embedded computer 230 controls the On-Off and mode switching of the energy generator 320 with the electromagnetic relay 321 to achieve On and mode switching of an energy input for the energy surgical actuator 383.

Figure 4:
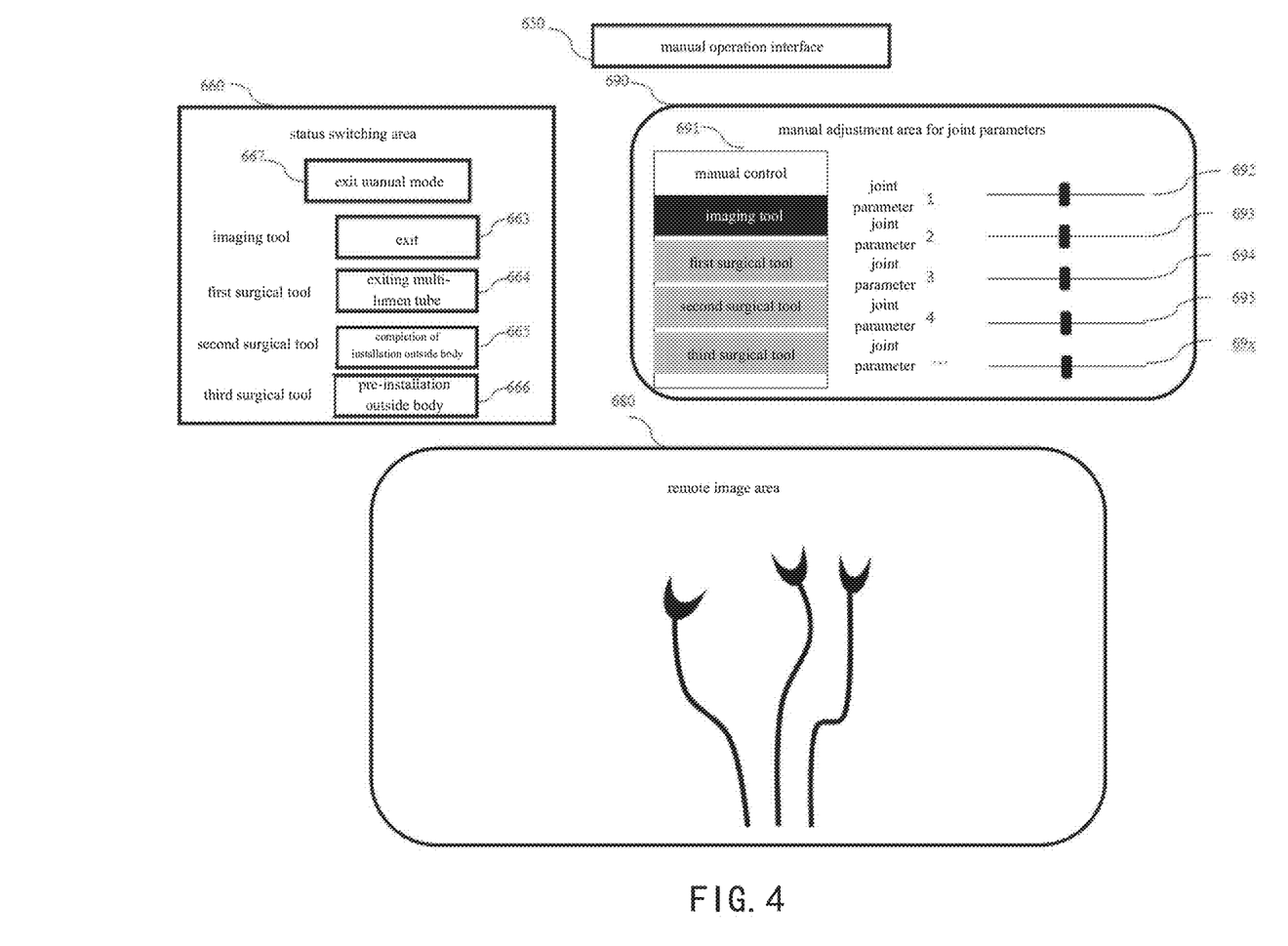
FIG. 4 is a schematic diagram of a manual operation interface of the present invention.

In the above embodiments, as shown in FIGS. 3 and 4, the operation interface 600 includes a status switching area 610, a status display area 620, a mapping selection area 630 and a remote image area 640.

The status switching area 610 includes a status inquiry button 611, a manual mode button 612, a status switching button 613 for imaging tool, and status switching buttons 614-616 for first to third surgical tools. When the status inquiry button 611 is activated, the host computer 130 transmits a status inquiry command to the embedded computer 230, and the embedded computer 230 transmits a status response instruction to the host computer 130 via the local area network router 210, the status response instruction represents the status of the integrated control system, the host computer 130 adjusts display options of the status switching buttons 614-616 for first to third surgical tools and the status switching button 613 for imaging tool according to the status response instruction, and changes contents displayed in the status display area 620. The manual mode button 612 can control the integrated control system to enter into a manual operating status and switch the operation interface 600 to the manual operation interface 650. The status switching button 613 for imaging tool is used to switch operating statuses of the imaging tool 362 and the imaging tool driving module 360. When the operator 101 clicks the status switching button 613 for imaging tool, a pull-down menu will be displayed, and the pull-down menu will display the statuses of all the imaging tools 362 and the imaging tool driving module 360 from which the operator 101 can select and switch to the corresponding status. The displayed status includes an initial status, a status of zero-return for imaging tool driving module, a status of pre-installation for imaging tool outside the body, a status for completion of installation for imaging tool outside the body, a status of entering/exiting surgical incision for the imaging tool and multi-lumen tube, a closed posture for imaging tool in the body, a status of advance expansion/retraction collapse of imaging tool, statuses of the imaging tool maintaining the current posture and the teleoperation motion of the imaging tool. The status switching buttons 614-616 for first to third surgical tools are used to switch the operational statuses of the first to third surgical tools 350-352 and the first to third surgical tool driving modules 330-332. When the operator 101 clicks the status switching button 614 for surgical tool, a pull-down menu will be displayed, and the pull-down menu will display the statuses of all the surgical tools 350 and the surgical tool driving module 330 from which the operator 101 can select and switch to the corresponding status. The displayed status includes an initial status, a status of zero-return for surgical tool driving module, a status of pre-installation for surgical tools outside the body, a status for completion of installation for surgical tools outside the body, a status of extending/retracting the surgical tool from/into the multi-lumen tube, a straight posture for surgical tools in the body, a status of expansion/back-straight of surgical tools, statuses of the surgical tools maintaining the current posture, electrocoagulation/electric cutting status under the teleoperation of the surgical tools and a status of the teleoperation motion of the surgical tools.

The status display area 620 includes status display frames 621-623 for first to third surgical tools and a status display frame 624 for imaging tool. The status display frames 621-623 for first to third surgical tools are respectively used to display current operating statuses of the first to third surgical tools 350-352 and the first to third surgical tool driving modules 330-332, respectively, the acquisition for the operating status information is achieved by the host computer 130 receiving the status instruction returned by the embedded computer 230 via the local area network router 210. The status display frame 624 for imaging tool is used to display current operating statuses of the imaging tool 362 and the imaging tool driving module 360, the acquisition for the operating status information is also achieved by the host computer 130 receiving the status instruction returned by the embedded computer 230 via the local area network router 210.

The mapping frame 630 includes a left-hand control frame 631 and a right-hand control frame 632. When the operator 101 selects a certain tool in the left-hand control frame 631, such as an imaging tool, at this time, the label corresponding to the imaging tool becomes dark, and the remaining labels in the left-hand control frame 631 are light colored (as shown in FIG. 3), and the remote control device 120 establishes a teleoperation mapping relationship with the imaging tool 632, i.e., the remote control device 120 can control motions of the imaging tool 362. Similarly, when the operator 101 selects a certain tool in the right-hand control frame 632, such as the second surgical tool 351, at this time, the label corresponding to the second surgical tool 351 becomes dark, and the remaining labels in the right-hand control frame 632 are light colored (as shown in FIG. 3), the remote control device 121 establishes a teleoperation mapping relationship with the second surgical tool 351, i.e., the remote control device 121 can control motions of the second surgical tool 351. It should be noted that each remote control device can only establish a mapping relationship with the imaging tool 362 or one surgical tool at the same time point. Therefore, the operator 101 can simultaneously control motions of the imaging tool 362 and one surgical tool or two surgical tools at most through two remote control devices 120, 121; the imaging tool or the surgical tool that does not establish a teleoperation mapping relationship with the two remote control devices 120, 121 is in a "keep current posture" state.

The remote image area 640 is used to display the image returned by the imaging illumination module 370.

In the above embodiments, as shown in FIG. 4, the manual operation interface 650 includes a status switching area 660, a remote image area 680, and a manual adjustment area 690 for joint parameters. The status switching area 660 includes an exit manual mode button 667, a status switching button 663 for imaging tool, and status switching buttons 664-666 for first to third surgical tools. The operating methods and functions of the status switching button 663 for imaging tool and the status switching buttons 664-666 for first to third surgical tools are consistent with those of the status switching button 613 for imaging tool and the status switching buttons 614-616 for first to third surgical tools in the operation interface 600. What make them different are that the pull-down menu of the status switching button 663 for imaging tool only provides a status of pre-installation for imaging tool outside the body, a status of completion of installation for imaging tool outside the body, a status of entering/exiting surgical incision for the imaging tool and the multi-lumen tube, a closed posture for imaging tool in the body, a status of advance expansion/retraction collapse of imaging tool for switching, the pull-down menus of the status switching buttons 614-616 for first to third surgical tools only provide a status of pre-installation for surgical tools outside the body, a status of completion of installation for surgical tools outside the body, a status of extending/retracting the surgical tool from/into the multi-lumen tube, a straight posture for surgical tools in the body, an expansion/back-straight status of surgical tools for switching. The exit manual mode button 667 can exit the manual operation interface 650 to the operation interface 600. The manual adjustment area 690 for joint parameters includes mapping selection area 691 and adjustment bars 692-69$x$ for joint parameters. In the mapping selection area 691, when a certain tool is selected, the corresponding label in the mapping selection area 691 becomes dark, and the respective black sliders in the parameter adjustment bars 692-69$x$ correspond to the parameter information of the corresponding joint, and the parameters can be adjusted by dragging the black sliders. The remote image area 680 is used to display the image returned by the imaging illumination module 370.

In the above embodiments, image signals of the imaging illumination module 370 can be transmitted to the display 110 through the local area network router 210, or can be transmitted through a dedicated video cable connected from the controlled terminal 200 to the main control terminal 100. The dedicated video cable can adopt HDMI video cable.

In a preferred embodiment, the present invention can achieve the selection of the teleoperation mappings between the two remote control devices 120-121 and the imaging tool 362, the first to third surgical tools 350-352 by adding multiple pedals. In this embodiment, the area where the two pedals 140, 141 are located may be divided into a left pedal area and a right pedal area, and the left pedal area includes a first pedal 140, a third surgical tool pedal, an imaging tool pedal, and correspondingly, a right pedal area includes a second pedal 141, a third surgical tool pedal, and an imaging tool pedal. The first pedal 140, the second pedal 141, the third surgical tool pedal, and the imaging tool pedal sequentially correspond to the first surgical tool 350, the second surgical tool 351, the third surgical tool 352, and the imaging tool 362, respectively. When any pedal in the left pedal area is depressed, a teleoperation mapping relationship between the remote control device 120 and the tool corresponding to the depressed pedal will be established, for example, if the third surgical tool pedal is depressed, the mapping relationship between the remote control device 120 and the third surgical tool 352 will be established; similarly, when any pedal in the right pedal area is depressed, the mapping relationship between the remote control device 121 and the tool corresponding to the depressed pedal is established. It should be noted that each remote control device can only establish a mapping relationship with one imaging tool 362 and one surgical tool at the same time point. Therefore, the operator 101 can simultaneously control the motions of the imaging tool 362 and one surgical tool or two surgical tools at most through the two remote control devices 120, 121.

In each of the above embodiments, the first to third indicator lights 340 to 342 and the indicator light for imaging 361 are used to display operating statuses of the first to third surgical tools 350-352 and the first to third surgical tool driving modules 330-332, the imaging tool 362 and the imaging tool driving module 360, the indications of their color are shown in Table 1 and Table 2.

TABLE 1 table for indications of status indicator 361 of imaging tool 362

| status of imaging tool 362 | color of indicator 361 |
|---|---|
| initial | white light is always on |
| zero-return for imaging tool driving module | yellow light is flashing quickly |
| pre-installation for imaging tool outside the body | yellow light is always on |
| completion of installation for imaging tool outside the body, illuminating and imaging entering/exiting surgical incision for imaging tool and multi-lumen tube | green light is breath-flashing |
| | green light is breath-flashing |
| a closed posture for imaging tool in the body | green light is breath-flashing |
| advance expansion/retraction collapse of imaging tool | green light is breath-flashing |
| the imaging tool maintaining the current posture | green light is flashing slowly |
| teleoperation motion of the imaging tool | green light is always on |
| manual operation | purple light is always on |
| error display status | red light is always on |

TABLE 2 table for indications of first to third status indicator lights 340-342 of first to third surgical tools 350-352

| status of first to third surgical tools 350-352 | color of first to third status indicator lights 340-342 |
|---|---|
| initial | white light is always on |
| zero-return for surgical tool driving module | yellow light is flashing quickly |
| pre-installation for surgical tools outside the body | yellow light is always on |
| completion of installation for surgical tools outside the body | green light is breath-flashing |
| extending/retracting the surgical tools from/into the multi-lumen tube | green light is breath-flashing |
| straight posture for the surgical tools in the body | green light is breath-flashing |
| expansion/back-straight of surgical tools | green light is breath-flashing |
| the surgical tools maintaining the current posture | green light is flashing slowly |
| teleoperation motion of the surgical tools | green light is always on |
| electrocoagulation/electric cutting of the surgical tools | blue light is always on |
| manual operation | purple light is always on |
| error display status | red light is always on |

Wherein, the yellow indicates pre-installation phase for the first to third surgical tools 350-352/imaging tool 362, and the quickly-flashing in this phase indicates that the first to third surgical tool driving modules 330-332/imaging tool driving module 360 are in an automated motion. In this embodiment, the display status of the yellow quickly-flashing may indicate the zero-return status of the imaging tool driving module and the zero-return state of the surgical tool driving modules; always on in this phase indicates that the first to third surgical tool driving modules 330-332 and the imaging tool driving module 360 are not in the automated motion. In the embodiment, the display status of yellow always on indicates pre-installation for imaging tool outside the body, pre-installation for surgical tool outside the body, the aforementioned automated motion refers to the first to third embedded computers 220-223 for surgical tools continuously send position control signals of the motor to the control module 3301.

Green indicates preparation/working phase for the first to third surgical tools 350-352/imaging tool 362, the breath-flashing in this phase indicates that the first to third surgical tools 350-352/imaging tool 362 are in manual or automated motion or gaps therebetween. In this embodiment, the display status of the green breath-flashing can indicate the completion of the installation for the imaging tool outside the body, the imaging tool and the multi-lumen tube entering into/exiting from the surgical incision, the closed posture of the imaging tool in the body, advance expansion/retraction collapse of the imaging tool, the completion of the installation for the surgical tool outside the body, the surgical tool entering into/exiting from the multi-lumen tubes, straight posture for the surgical tools in the body, expansion/back-straight of surgical tools; the slowly-flashing in this phase indicates that the first to third surgical tools 350-352/imaging tool 362 are in standby status under a teleoperation. In this embodiment, the display status of the green slowly-flashing can indicate that the imaging tool maintains the current posture and the surgical tool maintains the current posture; always-on in this phase indicates that the first to third surgical tools 350-352/imaging tool 362 are in working status under a teleoperation, in this embodiment, the display status of the green always-on can indicate teleoperation motion of the imaging tool and teleoperation motion of the surgical tools.

The difference between breath-flashing and slowly-flashing is that breath-flashing is slowly lit and extinguished; slowly-flashing are waiting for quickly lit, but with lower frequencies.

Blue represents the energy generation phase, which indicates that the energy generator 320 is outputting energy to the energy surgical actuator 383. In this embodiment, the display status of the blue may indicate electric cutting/electrocoagulation status of the surgical tools.

Red indicates that an error has occurred and the integrated control system of the present invention entering into a manual debugging phase.

The above embodiments are merely illustrative of the present invention, and the structure, size, arrangement position and shape of each component may be varied. On the basis of the technical solution of the present invention, improvements and equivalent transformations made to individual components according to the principles of the present invention should not be excluded from the scope of protection of the present invention.

The invention claimed is:

1. A control system for a surgical robot, the control system comprising:
   at least one first embedded computer connected with a surgical tool driving module or an imaging tool driving module of the surgical robot;
   a second embedded computer connected with the first embedded computer and configured to receive status information from the first embedded computer, the status information comprises a status of zero-return for the surgical tool driving module or the imaging tool driving module, and a status of extending/retracting the surgical tool or the imaging tool from/into a multi-lumen tube; and
   a host computer connected with the second embedded computer and configured to receive the status information from the second embedded computer;

wherein the surgical tool driving module or the imaging tool driving module comprises:
a controller;
a motor connected with a first coupling and configured to drive a surgical tool or an imaging tool via the first coupling by rotating the first coupling; and
a zero point switch configured to detect whether the first coupling is rotated to a rotational zero position;
wherein the controller is connected with the motor and the zero point switch, and configured to transmit the status of zero-return for the surgical tool driving module or the imaging tool driving module to the at least one first embedded computer based on whether the first coupling is rotated to the rotational zero position.

2. The control system of claim 1, wherein the surgical robot further comprises:
a surgical tool connected with the surgical tool driving module; or
an imaging tool connected with the imaging tool driving module.

3. The control system of claim 2, wherein the status information further comprises at least one of an initial status, a status of pre-installation for the surgical tool or the imaging tool, a status for completion of installation for the surgical tool or the imaging tool, a status of entering/exiting surgical incision for the multi-lumen tube, a closed posture for the imaging tool, a status of advance expansion/retraction collapse of the imaging tool, a status of the surgical tool or the imaging tool maintaining a current posture, a status of teleoperation motion of the surgical tool or the imaging tool, a straight posture for the surgical tool, a status of expansion/back-straight of the surgical tool, or electrocoagulation/electric cutting status under teleoperation of the surgical tool.

4. The control system of claim 2, wherein the surgical robot further comprises:
a sterile barrier disposed between the surgical tool driving module and the surgical tool or between the imaging tool driving module and the imaging tool.

5. The control system of claim 1, wherein the surgical robot further comprises:
a control device connected with the host computer and configured to control the surgical tool driving module or the imaging tool driving module based on a selection operation.

6. The control system of claim 5, wherein the control device is configured to trigger the host computer to send a status-changed signal to the first embedded computer or the second embedded computer.

7. The control system of claim 1, wherein the surgical tool driving module or the imaging tool driving module further comprises:
a reading chip configured to read information from a surgical tool connected with the surgical tool driving module or an imaging tool connected with the imaging tool driving module.

8. The control system of claim 7, wherein the surgical tool driving module or the imaging tool driving module further comprises:
a motor rotation angle sensor connected with the motor and configured to detect rotation of the motor;
wherein the controller is connected with the motor rotation angle sensor, and configured to control the motor based on a received control signal.

9. The control system of claim 7, wherein the surgical tool or the imaging tool comprises an information tag and a second coupling configured to be coupled with the first coupling, and the reading chip is configured to identify and read the information tag.

10. The control system of claim 7, wherein the controller connected with the first embedded computer through a first communication bus, and the reading chip is connected with the first embedded computer through a second communication bus.

11. The control system of claim 1, wherein the surgical robot further comprises:
a display connected with the host computer and configured to display the status information and receive an operation input from an operator.

12. The control system of claim 1, wherein the surgical robot further comprises:
one or more indicator lights connected with the second embedded computer through a third communication bus and configured to display an operating status.

13. The control system of claim 12, wherein the one or more indicator lights are disposed on the surgical tool driving module or the imaging tool driving module and configured to display an operating status of the surgical tool driving module, a surgical tool connected with the surgical tool driving module, the imaging tool driving module, or an imaging tool connected with the imaging tool driving module.

14. The control system of claim 13, wherein the operating status comprises a pre-installation phase of the surgical tool or the imaging tool, a preparation or working phase of the surgical tool or the imaging tool, an energy generation phase of an energy surgical actuator, an error, or a manual debugging phase.

15. The control system of claim 1, herein the surgical robot further comprises:
a local area network router connected with the host computer, the first embedded computer and the second embedded computer.

16. The control system of claim 1, wherein the surgical robot further comprises:
an electromagnetic relay connected with the second embedded computer through a fourth communication bus; and
an energy generator connected with the electromagnetic relay,
wherein the second embedded computer is configured to control the electromagnetic relay to control an energy surgery actuator connected with the energy generator and disposed on a surgical tool connected with the surgical tool driving module.

17. A surgical robot, comprising:
at least one surgical or imaging tool driving module;
at least one surgical or imaging tool connected with the surgical or imaging tool driving module;
at least one first embedded computer connected with the surgical or imaging tool driving module;
a second embedded computer connected with the first embedded computer and configured to receive status information from the first embedded computer, the status information comprises a status of zero-return for the surgical tool driving module or the imaging tool driving module, and a status of extending/retracting the surgical tool or the imaging tool from/into a multi-lumen tub; and
a host computer connected with the second embedded computer and configured to receive the status information from the second embedded computer and determine a status of the surgical or imaging tool extending from or retracting into the multi-lumen tube;
wherein the surgical tool driving module or the imaging tool driving module comprises:
a controller;
a motor connected with a first coupling and configured to drive a surgical tool or an imaging tool via the first coupling by rotating the first coupling; and
a zero point switch configured to detect whether the first coupling is rotated to a rotational zero position;
wherein the controller is connected with the motor and the zero point switch, and configured to transmit the status of zero-return for the surgical tool driving module or the imaging tool driving module to the at least one first embedded computer based on whether the first coupling is rotated to the rotational zero position.

18. The surgical robot of claim 17, wherein the host computer is further configured to determine a status of the multi-lumen tube entering or exiting into a surgical incision.

19. The surgical robot of claim 17, wherein the status information further comprises at least one of an initial status, a status of pre-installation for the surgical or imaging tool, a status for completion of installation for the surgical or imaging tool, a status of entering/exiting surgical incision for the multi-lumen tube, a closed posture for the imaging tool, a status of advance expansion/retraction collapse of the imaging tool, a status of the surgical or imaging tool maintaining a current posture, a status of teleoperation motion of the surgical or imaging tool, a straight posture for the surgical tool, a status of expansion/back-straight of the surgical tool, or electrocoagulation/electric cutting status under teleoperation of the surgical tool.

20. The surgical robot of claim 17, wherein the controller is connected with the first embedded computer through a first communication bus; and the surgical or imaging tool driving module further comprises:
a reading chip connected with the first embedded computer through a second communication bus and configured to read information from the surgical or imaging tool.

* * * * *